(12) United States Patent
Rourke et al.

(10) Patent No.: US 9,936,881 B2
(45) Date of Patent: Apr. 10, 2018

(54) POLARIZATION SCRAMBLING FOR INTRA-BODY FIBER OPTIC SENSOR

(71) Applicant: Vascular Imaging Corporation, Rancho Cordova, CA (US)

(72) Inventors: Howard Neil Rourke, Sacramento, CA (US); Michael J. Eberle, Fair Oaks, CA (US); Shukui Zhao, Folsom, CA (US); Diana Margaret Tasker, Fair Oaks, CA (US)

(73) Assignee: Vascular Imaging Corporation, Rancho Cordova, CA (US)

( * ) Notice: Subject to any disclaimer, the term of this patent is extended or adjusted under 35 U.S.C. 154(b) by 0 days.

(21) Appl. No.: 14/045,189

(22) Filed: Oct. 3, 2013

(65) Prior Publication Data

US 2014/0100462 A1    Apr. 10, 2014

Related U.S. Application Data

(60) Provisional application No. 61/709,700, filed on Oct. 4, 2012.

(51) Int. Cl.
*A61B 5/00* (2006.01)
*A61B 8/12* (2006.01)
(Continued)

(52) U.S. Cl.
CPC ........ *A61B 5/0095* (2013.01); *A61B 5/02007* (2013.01); *A61B 8/12* (2013.01); *G01D 5/35354* (2013.01)

(58) Field of Classification Search
CPC .............. G01D 5/35354; A61B 5/0095; A61B 5/02007; A61B 8/12
See application file for complete search history.

(56) References Cited

U.S. PATENT DOCUMENTS 3,995,623 A    12/1976 Blake et al.
4,917,097 A    4/1990 Proudian et al.
(Continued)

FOREIGN PATENT DOCUMENTS

EP           1238264 B1    12/2004
WO    WO-2015051003 A1    4/2015

OTHER PUBLICATIONS

"International Application Serial No. PCT/US2013/063212, International Search Report dated Jan. 16, 2014", 5 pgs.
(Continued)

*Primary Examiner* — Long V Le
*Assistant Examiner* — Colin T Sakamoto
(74) *Attorney, Agent, or Firm* — Schwegman Lundberg & Woessner, P.A.

(57) ABSTRACT

In an example, an optical system can include a polarization scrambler coupleable to a tunable first optical source configured to generate a coherent optical output. The system can include an intra-body optical sensor such as a an intravascularly-deliverable optical fiber transducer, configured to be coupled to the tunable first optical source through the polarization scrambler, the polarization scrambler configured to vary a polarization state of the optical energy provided by the tunable first optical source, the intravascularly-deliverable optical fiber transducer configured to reflect a portion of the optical energy modulated in response to a vibration, pressure, or strain. The system can include a processor circuit configured to obtain information indicative of the optical energy reflected from the intravascularly-deliverable optical fiber transducer, and to process information from the vibration, pressure, or strain modulating the optical energy from the intravascularly-deliverable optical fiber transducer using different polarization states established by the polarization scrambler.

19 Claims, 6 Drawing Sheets

(51) Int. Cl.
*A61B 5/02* (2006.01)
*G01D 5/353* (2006.01)

(56) References Cited

U.S. PATENT DOCUMENTS

| | | | |
|---|---|---|---|
| 5,167,233 | A | 12/1992 | Eberle et al. |
| 5,325,860 | A | 7/1994 | Seward et al. |
| 5,603,327 | A | 2/1997 | Eberle et al. |
| 5,873,835 | A | 2/1999 | Hastings et al. |
| 6,049,958 | A | 4/2000 | Eberle et al. |
| 6,337,737 | B1 | 1/2002 | Chang et al. |
| 6,659,957 | B1 | 12/2003 | Vardi et al. |
| 6,938,474 | B2 | 9/2005 | Melvås |
| 7,097,620 | B2 | 8/2006 | Corl et al. |
| 7,245,789 | B2 | 7/2007 | Bates et al. |
| 7,447,388 | B2 | 11/2008 | Bates et al. |
| 7,527,594 | B2 | 5/2009 | Vardi et al. |
| 7,660,492 | B2 | 2/2010 | Bates et al. |
| 7,753,852 | B2 | 7/2010 | Maschke |
| 8,059,923 | B2 | 11/2011 | Bates et al. |
| 2002/0041735 | A1 | 4/2002 | Cai et al. |
| 2002/0059827 | A1 | 5/2002 | Smith |
| 2003/0175034 | A1 | 9/2003 | Noe |
| 2004/0067000 | A1 | 4/2004 | Bates et al. |
| 2005/0121734 | A1 | 6/2005 | Degertekin et al. |
| 2005/0200855 | A1 | 9/2005 | Mcinnes et al. |
| 2005/0200941 | A1 | 9/2005 | Yao |
| 2005/0232531 | A1 | 10/2005 | Hadley et al. |
| 2008/0119739 | A1 | 5/2008 | Vardi et al. |
| 2012/0108943 | A1 | 5/2012 | Bates et al. |
| 2014/0180031 | A1 | 6/2014 | Anderson |
| 2014/0180034 | A1 | 6/2014 | Hoseit et al. |
| 2014/0200438 | A1 | 7/2014 | Millett et al. |
| 2016/0242653 | A1 | 8/2016 | Rourke et al. |

OTHER PUBLICATIONS

"International Application Serial No. PCT/US2013/063212, Written Opinion dated Jan. 16, 2014", 7 pgs.

Siebes, M., et al., "Single-Wire Pressure and Flow Velocity Measurement to Quantify Coronary Stenosis Hemodynamics and Effects of Percutaneous Interventions", *Circulation*, 109, (2004), 756-762.

"Scrambling to Reduce Polarization Related Impairments, Application Note", General Photonics Corporation, (Apr. 2003), 4 pgs.

"European Application Serial No. 13779472.3, Office Action dated May 18, 2015", 2 pgs.

"European Application Serial No. 13779472.3, Response filed Nov. 16, 2015 to Office Action dated May 18, 2015", 14 pgs.

International Application Serial No. PCT/US2013/063212, International Preliminary Report on Patentability dated Apr. 16, 2015, 9 pgs.

"European Application Serial No. 13779472.3, Office Action dated May 10, 2016", 7 pgs.

"European Application Serial No. 13779472.3, Respose filed Sep. 19, 2016 to Office Action dated May 10, 2016", 17 pgs.

U.S. Appl. No. 15/026,521, Preliminary Amendment filed Mar. 31, 2016, 3 pgs.

International Application Serial No. PCT/US2014/058643, International Search Report dated Jan. 19, 2015, 3 pgs.

International Application Serial No. PCT/US2014/058643, Written Opinion dated Jan. 19, 2015, 6 pgs.

U.S. Appl. No. 15/026,521, filed Mar. 31, 2016, Imaging Techniques Using an Imaging Guidewire.

"European Application Serial No. 13779472.3, Office Action dated Aug. 2, 2017", 5 pgs.

POLARIZATION SCRAMBLING FOR INTRA-BODY FIBER OPTIC SENSOR

CLAIM OF PRIORITY

This application claims the benefit of priority of U.S. Provisional Patent Application Ser. No. 61/709,700, titled "POLARIZATION SCRAMBLING FOR INTRA-BODY FIBER OPTIC SENSOR," by Rourke et al., and filed on Oct. 4, 2012, which is herein incorporated by reference in its entirety.

BACKGROUND

Interventional medical procedures are increasingly relied upon to treat patients suffering from coronary artery disease or cardiac ischemia. In particular, such patients may be treated using vascular bypass operations such as Coronary Artery Bypass Graft (CABG), or less invasive techniques. Less invasive techniques may include one or more of angioplasty or stenting, which can be referred to generally as Percutaneous Coronary Intervention (PCI), or atherectomy, brachytherapy, or one or more other techniques. Such less invasive techniques often include introduction of one or more catheters or guidewires into the vasculature. Similar approaches can be used for treating various symptoms or diseases involving other physiologic locations (e.g., a biliary location, a carotid artery location, or one or more other locations). Various imaging techniques can provide useful feedback to a caregiver before, during, or after an intravascular or intraluminal procedure. Such imaging techniques can include X-ray (e.g., fluoroscopy) or ultrasound-based techniques.

Vardi and Spivak, U.S. Pat. Nos. 6,659,957, 7,527,594, and U.S. Pat. Pub. No. US-2008-0119739-A1, each of which is hereby incorporated by reference herein in its entirety, describe, among other things, an elongated imaging apparatus, for internal patient imaging, the apparatus including an electrical-to-acoustic transmit transducer and an acoustic-to-optical receive transducer.

Bates and Vardi, U.S. Pat. No. 7,245,789, 7,447,388, 7,660,492, 8,059,923, and U.S. Pat. Pub. No. US-2012-0108943-A1, each of which is hereby incorporated by reference herein in its entirety, describe, among other things, an elongated imaging apparatus, for internal patient imaging, the apparatus including an optical-to-acoustic transmit transducer and an acoustic-to-optical receive transducer.

Overview

An optical fiber transducer can be configured to couple optical energy from an optical source to a sensing region along the transducer. The sensing region along the transducer can include an interferometer structure. The optical fiber transducer can be sized and shaped for intravascular use or for use in one or more other body lumens or locations.

Optical energy coupled to the interferometer structure can be modulated or otherwise adjusted in relation to one or more physiologic parameters (e.g., modulated by a pressure), or in relation a received acoustic energy (e.g., ultrasonic energy) or mechanical vibration. The optical fiber transducer can be included as a portion of a guidewire assembly. Ultrasound-based imaging or sensing, such as using the optical fiber transducer, can provide a variety of advantages as compared to other imaging or sensing techniques, or can complement other techniques. Unlike X-ray imaging techniques, ultrasound is an acoustic technique and is therefore non-ionizing.

A pressure or vibration coupled to a sensing region of the optical fiber transducer can induce a change in the refractive index of the optical fiber transducer, or can physically modulate an optical path length of optical energy within the interferometer, causing a detectable change in a reflected intensity of the optical energy. The modulated reflected optical energy from the interferometer can be coupled back to a detector, and processed, such as to determine one or more physiologic parameters or to construct an image.

The present inventors have recognized, among other things, that optical materials, including optical fibers, generally possess some degree of birefringence. Such birefringence can cause unwanted distortion of optical energy coupled through the optical fiber transducer. Such distortion can include unwanted variation in a time-domain intensity profile of optical energy reflected from the interferometer structure. For example, as a caregiver or other user manipulates a guidewire including an optical fiber transducer (e.g., twisting, rotating, bending, compressing, or tensioning the guidewire), a propagation axis of optical energy in the optical fiber can be shifted, a polarization state of propagating optical energy can be shifted, or an index of refraction can be shifted non-uniformly across different polarization axes. Variation in the input polarization state of optical energy coupled into the fiber can also be a source of variation in the reflected response from the interferometer structure.

The present inventors have recognized, among other things, that an optical fiber transducer assembly (e.g., an imaging guidewire assembly) can include one or more unusually small optical fibers such as to provide imaging or sensing, along with over-the-wire access to the site of the imaging guidewire assembly in situ without requiring removal, retraction, or exchange of the imaging guidewire assembly. For example, the optical fiber transducer can include an outer diameter in a range of about 25 micrometers to about 30 micrometers, instead of a more typical telecommunication optical fiber outer diameter of about 125 micrometers. Even such an unusually small fiber diameter can magnify the effect of unwanted polarization-related distortion because the fiber diameter is comparable to an ultrasound wavelength for applications using an ultrasound frequency in the range of tens of megahertz (MHz), such as about 50 MHz.

In an ultrasonic application, a phase shift in optical energy within the fiber induced by the ultrasonic energy can vary non-monotonically with respect to a wavelength of the ultrasonic energy as a radius of the optical fiber transducer approaches the wavelength of acoustic energy. The phase shift can also vary significantly depending on the polarization state of the optical energy propagating in the fiber or the phase of the incident ultrasonic energy.

Accordingly, the present inventors have recognized, among other things, that an input polarization state of the optical energy can be controllably varied. In an ultrasonic application, the polarization state of optical energy coupled into the optical fiber can be different, such as for successive measurement durations. One or more of an average or other central tendency of detected information representative of the reflected optical energy can be determined, and a variation induced by birefringence or sources of polarization-related phase distortion can be reduced or eliminated. In a pressure-sensing application, for example, a measurement duration (e.g., a measurement window) can be specified so that a variety of input polarization states are provided during the measurement duration.

In an example, an optical system can include a polarization scrambler configured to be coupleable to a tunable first optical source configured to generate a coherent optical output including optical energy having a specified tunable wavelength. The system can include an intra-body optical sensor such as a an intravascularly-deliverable optical fiber transducer, configured to be coupled to the tunable first optical source through the polarization scrambler, the polarization scrambler configured to vary a polarization state of the optical energy provided by the tunable first optical source, the intravascularly-deliverable optical fiber transducer configured to reflect a portion of the optical energy modulated in response to a vibration, pressure, or strain. The system can include a processor circuit configured to obtain information indicative of the optical energy reflected from the intravascularly-deliverable optical fiber transducer, and to process information from the vibration, pressure, or strain modulating the optical energy from the intravascularly-deliverable optical fiber transducer using different polarization states established by the polarization scrambler.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
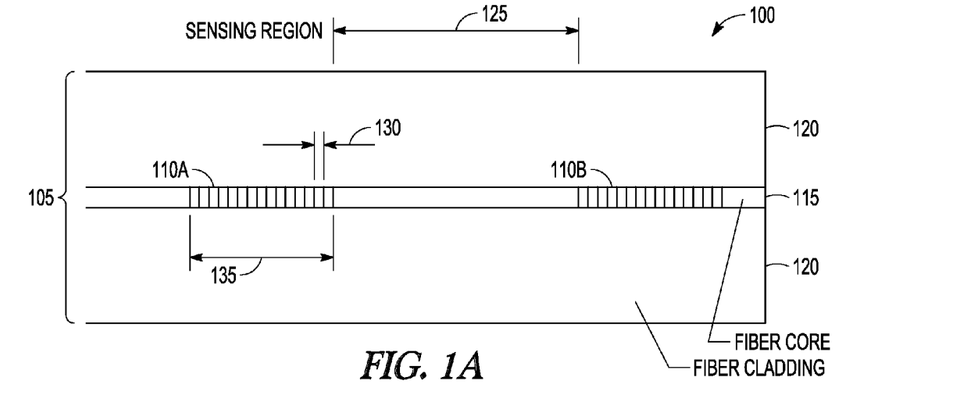
FIG. 1A illustrates generally an example that can include a portion of an optical fiber transducer, such as sized and shaped for delivery to an intravascular location.

FIG. 1A illustrates generally an example that can include a portion of an optical fiber transducer 100, such as sized and shaped for delivery to an intravascular location. The optical fiber transducer 100 can include an optical fiber assembly 105, such as including an optical fiber core 115 and a cladding 120. The optical fiber transducer 100 can include an interferometer structure, such as comprising one or more Fiber Bragg Gratings (FBGs). An FBG can be configured to reflect a specified proportion of incident optical energy for a specified range of wavelengths, similarly to a mirror.

A first FBG 110A can be located along the optical fiber core. The first FBG 110A can include a specified or periodic variation in the index of refraction along a long axis of the optical fiber core 115. For example, the optical fiber core 115 can have a first index of refraction, and the first FBG 110A can include portions having a second index of refraction "written" or otherwise impressed in the optical fiber core 115 in a periodic configuration, such as having a spacing between the portions having the second index that can be referred to as the period 130 of the first FBG 110A. The first and second indices of refraction, and the period 130 of the first FBG 110A, can be used to control a range of wavelengths for which the first FBG 110A is reflective. The first and second indices of refraction and an axial length 135 of the first FBG 110A can be used to control a proportion of incident optical energy that is reflected versus transmitted through the first FBG 110A. A second FBG 110B can be located along the fiber core 115, such as separated from the first FBG 110A by a sensing region 125. A combination of the first and second FBGs 110A and 110B can establish an interferometer structure (e.g., a Fabry-Perot cavity).

Figure 1B:
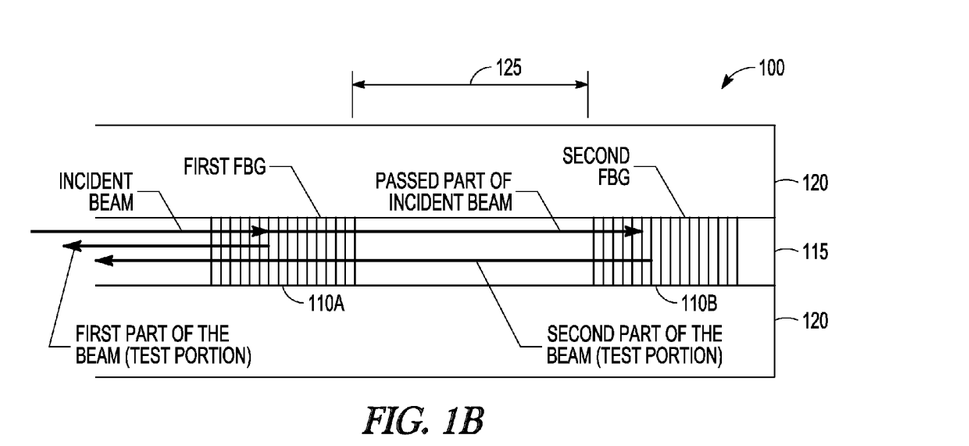
FIG. 1B illustrates generally an example that can include a portion of an optical fiber transducer, such as sized and shaped for delivery to an intravascular location.

As shown in FIG. 1B, incident optical energy (e.g., an incident beam) can be coupled to the interferometer structure established by the first and second FBGs 110A and 110B. Such optical energy can be generated by a first optical source, such as a laser. Along the length of the optic fiber transducer, the first FBG 110A can be located more proximally to the first optical source than the second FBG 110B.

A portion of the incident optical energy can be reflected by the first FBG 110A (e.g., a "first part of the beam") and from the second FBG 110B (e.g., a "second part of the beam"). A phase relationship between the reflected portions of the optical energy can be adjusted such as by any change affecting the optical path length between the first and second FBGs 110A and 110B, such as an optical path including the sensing region 125. Such a change in optical path length can occur when one or more vibration, pressure, or strain is imparted on the optical fiber core 115 such as via the cladding 120, causing a change in the index of refraction of the optical fiber core 115 in the sensing region 125 or a physical lengthening or shortening the optical path in the sensing region 125. Such variation in the optical path length in the sensing region 125 can modulate or adjust an intensity of optical energy reflected from the interferometer structure. In this manner, the optical fiber transducer 100 can be configured to provide an acousto-optical transducer.

Figure 2:
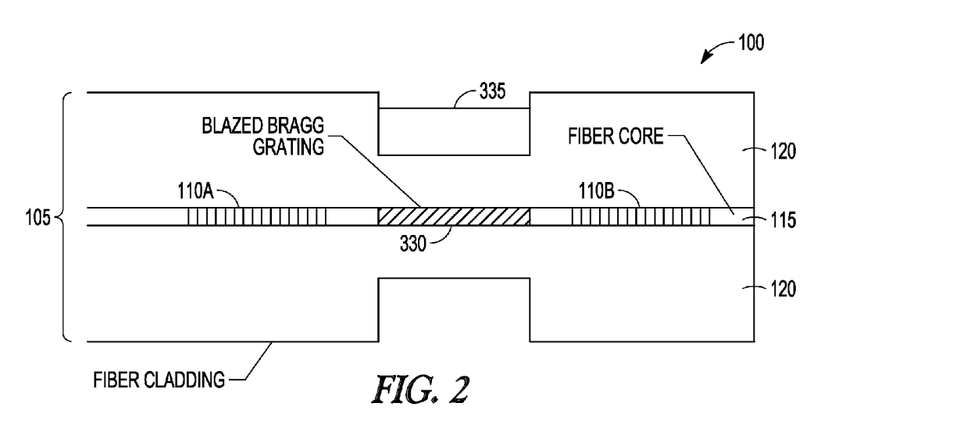
FIG. 2 illustrates generally an example that can include a portion of an optical fiber transducer, such as including a blazed grating structure, such as configured for use with an ultrasound technique.

FIG. 2 illustrates generally an example that can include a portion of an optical fiber transducer 100, such as can include a "blazed" grating structure 330, such as configured for use with an ultrasound technique. As in the examples of FIGS. 1A and 1B, the optical fiber transducer 100 can be intravascularly deliverable, such as including an optical fiber assembly 105 including an optical fiber core 115, a cladding 120, and one or more FBGs such as first FBG 110A or a second FBG 110B. The first or second FBGs 110A or 110B can generally include a specified or periodically-varying index of refraction, with the index of refraction homogeneous in the radial direction, and varying in the axial direction along a longitudinal axis of the optical fiber core 115. In the example of FIG. 2, a "blazed" FBG can be included, such as having an index of refraction impressed obliquely at a non-perpendicular angle to the longitudinal axis of the optical fiber core 115.

Such a blazed grating structure 330 can be used to outcouple optical energy from the optical fiber core 115. In an example, optical energy can be provided to the blazed grating structure 330 such as coupleable to an optically-absorptive photoacoustic material 335. Such an optically-absorptive photoacoustic material 335 can be specified to expand in the presence of intense optical energy, and can abruptly contract as the optical energy outcoupled from the optical fiber core 115 is reduced or suppressed, such as to provide an ultrasonic wave or other mechanical wave or vibration without requiring an electrically-driven transducer in the optical fiber transducer 100. Reflected acoustic or mechanical energy can then be sensed using an interferometer configuration including the first and second FBGs 110A and 110B, as discussed above in the examples of FIGS. 1A and 1B.

Figure 3:
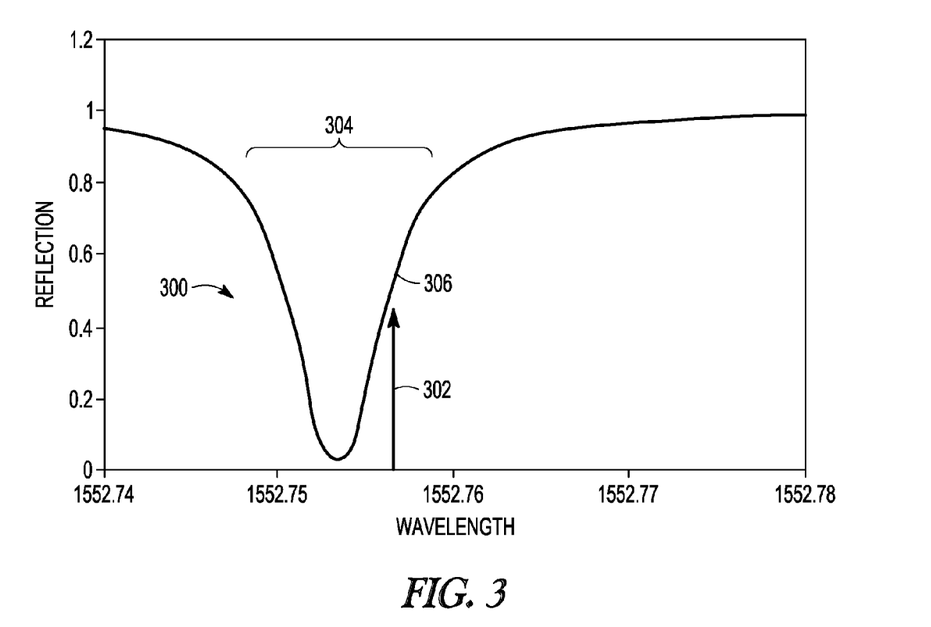
FIG. 3 illustrates generally an illustrative example of optical energy, such as can be reflected from an interferometer structure.

FIG. 3 illustrates generally an illustrative example 300 of optical energy, such as can be reflected from an interferometer structure, such as shown and described in one or more of the examples of FIGS. 1A or 1B, FIG. 2, FIG. 4, or FIG. 7 or 8. In the example of FIG. 3, an interferometer structure (e.g., a Fabry-Perot cavity) can provide one or more transmission features, such as a null 304 established by an optical path length between respective FBG structures. As an optical path length between the respective FBG structures varies (e.g., due to an impressed vibration, pressure, or strain), a location of the null 304 can shift in wavelength.

A tunable optical source can provide an output wavelength 302 locked to a specified region 306 of the null 304, such as to provide a desired or specified level of sensitivity to shifts in the null 304 location. Such wavelength shifts of the null 304 can be converted into variations in the amplitude or intensity of reflected optical energy (e.g., amplitude modulating the incident optical energy to provide the reflected optical energy) because the output wavelength 302 of the tunable optical source can remain roughly constant during such shifts.

The tunable optical source (e.g., a laser coupled to an optical fiber transducer) can be controlled in part using a feedback loop configured to adjust an output wavelength 302 of the tunable optical source to keep the wavelength 302 of the tunable optical source aligned with the specified region 306 of the null 304 as the null 304 shifts for reasons not related to physiologic information of interest. For example, in an acoustic (e.g., ultrasound) or mechanical vibration sensing application, a loop bandwidth of one or more such feedback loops can be established below a frequency range corresponding to received acoustic or mechanical vibrational energy, so that the optical energy source tracks shifts in the null 304 location that are unrelated to the acoustic or mechanical vibrational energy. For frequencies above the specified loop bandwidth, the output wavelength 302 of the tunable optical source can remain roughly constant, and the null 304 location can shift around the output wavelength 302 in response to the coupled acoustic or mechanical vibrational energy and thereby can modulate the optical energy reflected by the transducer.

In an illustrative example, the output wavelength 302 can be locked to a specified region 306 about halfway along a transition between relative minimum intensity of the optical energy reflected from the transducer and a relative maximum intensity of the optical energy reflected from the transducer. In another illustrative example, the output wavelength 302 can be locked to a region of about 30 to about 40 percent of the difference between the relative maximum intensity and the relative minimum intensity of the reflected optical energy.

Figure 4:
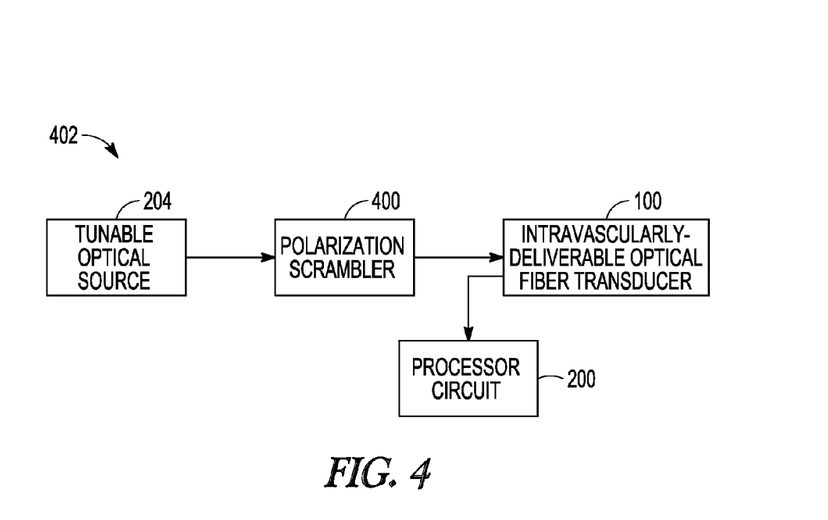
FIG. 4 illustrates generally an example of a system that can include an intravascularly-deliverable optical fiber transducer.

FIG. 4 illustrates generally an example of a system 402 that can include an intravascularly-deliverable optical fiber transducer 100, such as shown and described in the examples of FIGS. 1A and 1B, FIG. 2, and elsewhere. The system can include a tunable optical source 204, such as coupled to the intravascularly-deliverable optical fiber transducer 100, such as through or otherwise using a polarization scrambler 400. As discussed in the examples above and below, the tunable optical source 204 can be configured to provide optical energy at a specified output wavelength, and the intravascularly-deliverable optical fiber transducer 100 can modulate or otherwise adjust an intensity of the optical energy reflected from the intravascularly-deliverable optical fiber transducer 100. Information indicative of such reflected optical energy can be provided to a processor circuit 200, such as to process information indicative of a vibration, pressure, or strain modulating the optical energy.

A variety of techniques can be used to one or more of rotate or transform a polarization of the optical energy coupled from the tunable optical source 204 to the intravascularly-deliverable optical fiber transducer 100. For example, the polarization scrambler 400 can include one or more electro-optical materials, such as a one or more electro-optical waveplates as shown and described in the example below of FIG. 7. The polarization scrambler 400 can include one or more piezoelectric devices, such as configured to controllably elongate an optical fiber coupled to the piezoelectric device and thereby manipulate the polarization of optical energy propagating through the optical fiber.

Figure 5:
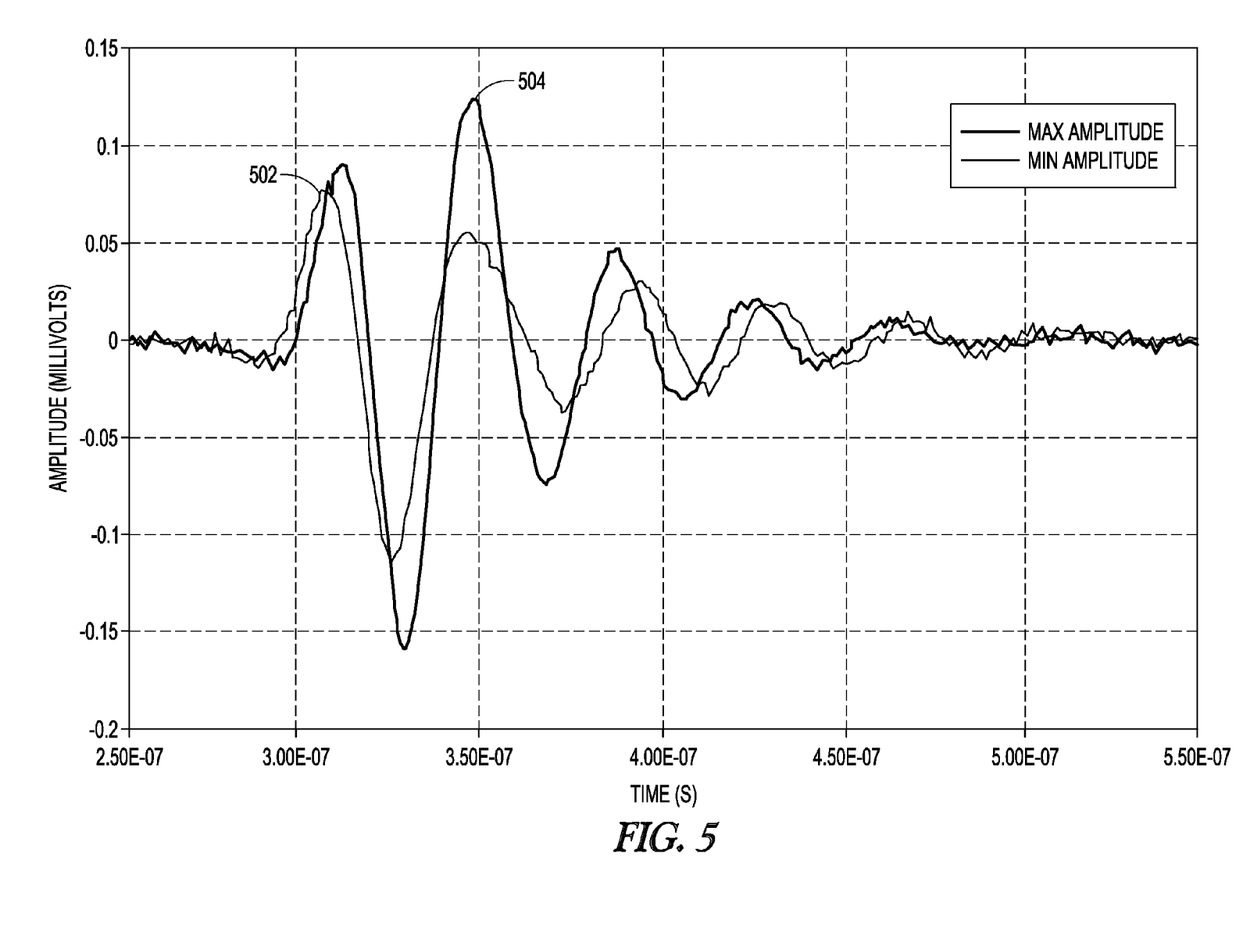
FIG. 5 illustrates generally experimentally-obtained time-domain representations of optical energy reflected from an interferometer structure.

As discussed above, optical materials, including optical fibers, generally have some degree of birefringence. Such birefringence can cause unwanted distortion or variation in the optical energy reflected from an interferometer located along an optical fiber transducer. Such distortion can include unwanted variation in a time-domain intensity profile of optical energy reflected from an interferometer structure included as a portion of the intravascularly-deliverable optical fiber transducer 100, such as shown in FIG. 5. Accordingly, the present inventors have recognized, among other things, that an input polarization state of the optical energy can be controllably varied such as using the polarization scrambler 400.

FIG. 5 illustrates generally experimentally-obtained time-domain representations of optical energy reflected from an interferometer structure included as a portion of an optical fiber, such as including an illustrative example of unwanted variation between such time-domain representations corresponding to different configurations of the optical fiber as manipulated by a user. First and second acquisitions 502 and 504 correspond to time-domain electrical signals obtained using an optical detector and indicative of the amplitude of the optical energy reflected from the interferometer structure.

The first acquisition 502 includes an amplitude that peaks during a first cycle of the first acquisition 502 time-domain waveform. A second acquisition 504 includes an amplitude that peaks a second cycle of the second acquisition 504 time-domain waveform. The second acquisition 504 also appears to include a cycle length that is compressed during certain cycles as compared to the first acquisition 504, indicating that the polarization-induced distortion affects not just an amplitude of received optical energy, but can also cause phase distortion over a duration of an acquisition.

In an illustrative example, the optical energy can be provided by a tunable optical source (e.g., a laser) at an output wavelength of about 1550 nanometers. A polarization-induced shift in optical path length can correspond to a variation on the order of parts-per-million. For a 1550 nanometer wavelength, such a path length variation can correspond to picometers of variation. Such variation can be significant in relation to variation in the optical path length induced in the interferometric cavity by effects of interest such as physiologically-related pressure, vibration, or strain. As shown in FIG. 5, a magnitude of a difference between peak amplitudes of the first and second acquisitions 502 and 504 is a significant proportion of the total signal amplitude, showing that such distortion can adversely impact usable dynamic range, contrast, clarity, or stability of obtained imaging or sensing information in the absence of polarization scrambling.

Figure 6A:
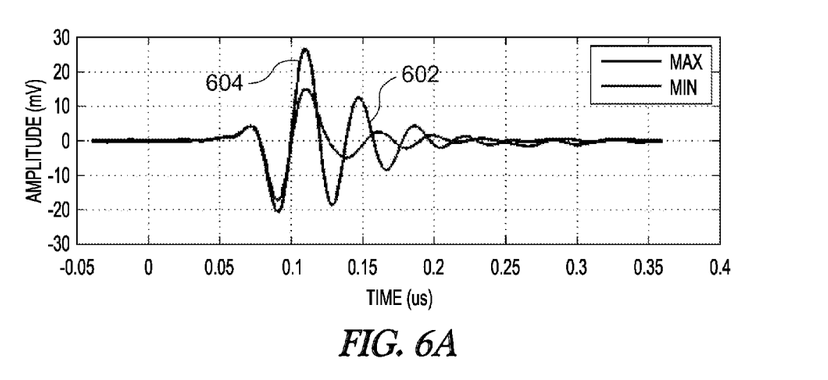
FIGS. 6A and 6B illustrate generally a comparison between experimentally-obtained time-domain representations of optical energy reflected from an interferometer structure without polarization scrambling enabled (e.g., FIG. 6A) and with polarization scrambling enabled (e.g., FIG. 6B).
Figure 6B:
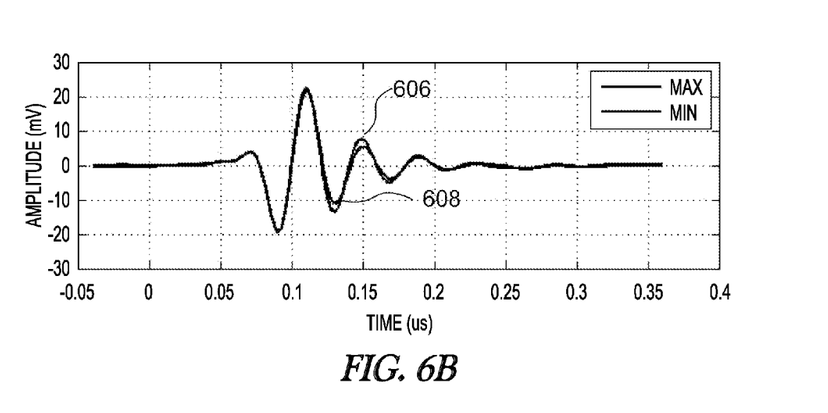
Figure 7:
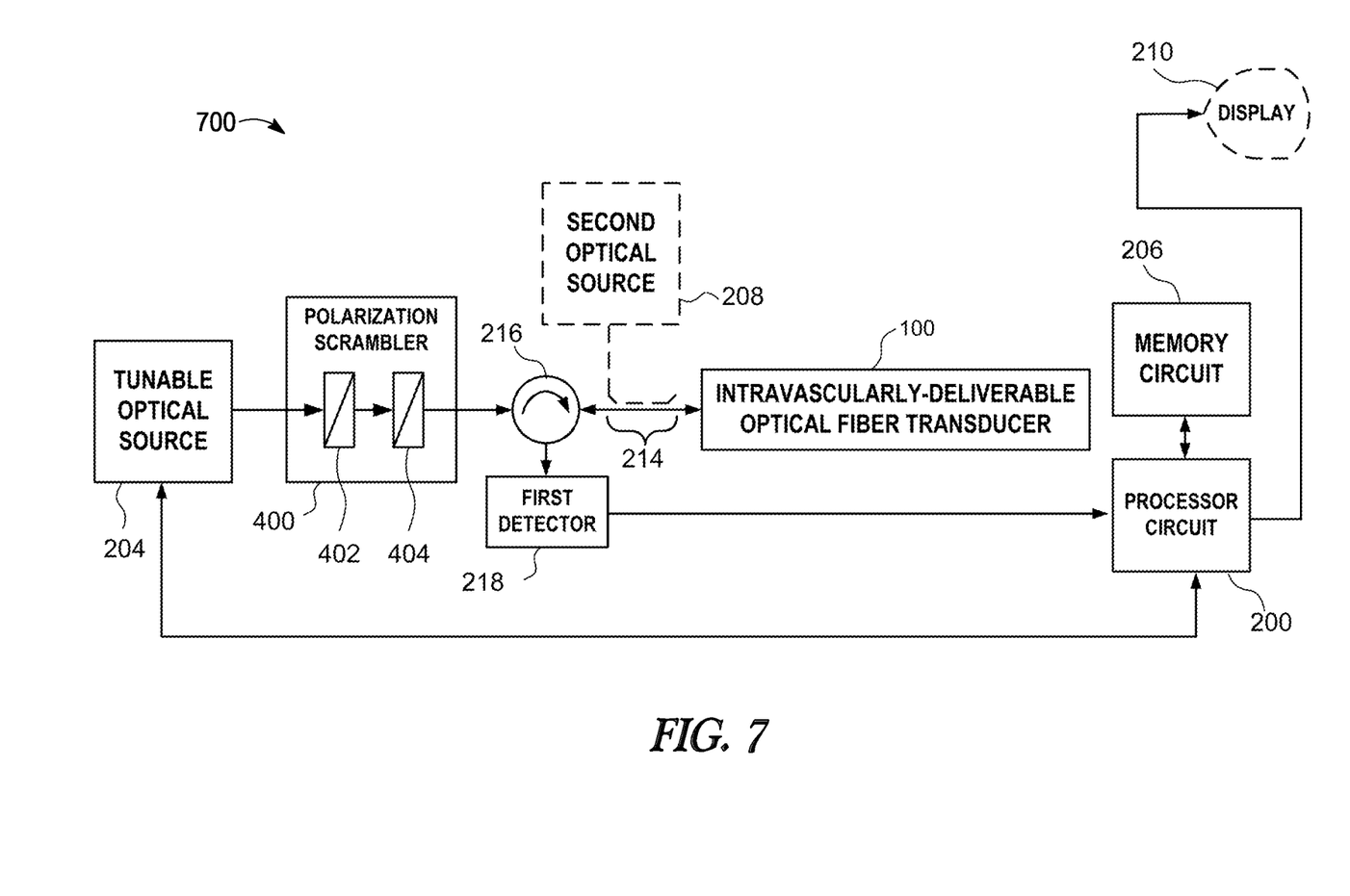
FIG. 7 illustrates generally an example of a system that can include an intravascularly-deliverable optical fiber transducer.

FIGS. 6A and 6B illustrate generally a comparison between experimentally-obtained time-domain representations of optical energy reflected from an interferometer structure without polarization scrambling enabled (e.g., FIG. 6A) and with polarization scrambling enabled (e.g., FIG. 6B), such as can be obtained using a polarization scrambler 400 configuration as shown in the example of FIG. 7 (e.g., including a polarization rotator and a polarization transformer).

In FIG. 6A, similarly to the example of FIG. 5, a first acquisition 602 and a second acquisition 604 show significant variation between each other, such as corresponding to different configurations of the optical fiber as manipulated by a user. As in the example of FIG. 5, such variation can occur both in amplitude and cycle length. In FIG. 6B, polarization scrambling can be enabled. A variation between a third acquisition 606 and a fourth acquisition 608 can be substantially reduced or eliminated using polarization scrambling, despite manipulation of the optical fiber by the user.

FIG. 7 illustrates generally an example of a system 700 that can include an intravascularly-deliverable optical fiber transducer 100. A tunable optical source 204 can be coupled to the intravascularly-deliverable optical fiber transducer 100, such as through or otherwise using a polarization scrambler 400. Reflected optical energy modulated or adjusted by the intravascularly-deliverable optical fiber transducer 100 can be coupled back to first detector 218, such as through a circulator 216. Information indicative of the reflected optical energy can be provided to a processor circuit 200, such as for storage in a memory circuit 206. The processor circuit 200 can be configured to process information from the reflected optical energy indicative of one or more of a vibration, pressure, or strain impressed upon or otherwise coupled to a sensing region of the intravascularly-deliverable optical fiber transducer 100, such as to determine one or more physiologic parameters or to construct an image of a physiologic region nearby the sensing region. Such physiologic parameters or imaging information can be presented to a user using a display 210.

In a mechanical vibration or acoustic (e.g., ultrasound) sensing application, a second optical source 208 can be included. The second optical source 208 can be configured for pulsed operation, such as including an optical output energy level higher than the level provided by the tunable optical source 204. The second optical source can be coupled to the intravascularly deliverable optical fiber transducer 100 such as using a combiner 214. The second optical source 208 can be configured to generate a coherent optical output including optical energy having a different wavelength than a wavelength provided by the first optical source. For example, the second optical source can be configured to generate optical energy at a wavelength of about 1060 nm as compared to the tunable optical source 204, which can be configured to generate optical energy at wavelengths around 1550 nm.

A region of tissue can be insonified, such as using energy obtained optically from the second optical source 208, such as discussed in relation to the example of FIG. 2 (e.g., using a blazed FBG to couple the optical energy to a photo-acoustic material). In response, acoustic energy reflected from the insonified region of tissue can be detected using the tunable optical source 204 to probe the intravascularly-deliverable optical fiber transducer 100, such as using the intravascularly-deliverable optical fiber transducer 100 to modulate or adjust the reflected optical energy, which can be detected by the first detector 218 and processed by the processor circuit 200. Acoustic energy used to insonify the region of tissue can include a center frequency of between about 5 MHz and about 50 MHz, or one or more other ranges of frequencies.

As discussed above, the polarization scrambler 400 can use various approaches to one or more of transform or rotate a polarization of optical energy provided by the tunable optical source 204. The second optical source 208 need not use the polarization scrambler 400 because the second optical source 208 is used to provide optical energy that can be used for generation of acoustic energy, rather than for sensing reflected acoustic or vibrational energy, or because the second optical source 208 can use a different range of wavelengths than the tunable optical source 204.

In an illustrative example, such as shown in FIG. 7, the polarization scrambler 400 can include a polarization rotator 402 and a polarization transformer 404. In FIG. 7, the polarization rotator 402 is shown as more proximally located to the tunable optical source 204 in comparison to the polarization transformer 404. However, the order of the polarization rotator 402 and the polarization transformer 404 can be switched and need not be arranged as shown in the FIG. 7. In an illustrative example, one or more of the polarization rotator 402 or the polarization transformer 404 can include a waveplate, such as comprising an electro-optical device having a birefringence or other property controllable at least in part using an electrical signal.

The polarization rotator 402 can include a half-wavelength waveplate configured to controllably shift (e.g., rotate) a polarization direction of optical energy propagating through the waveplate. The polarization transformer 404 can include a quarter-wavelength waveplate configured to transform a portion of linearly-polarized optical energy propagating through the waveplate into circularly-polarized optical energy, or to transform a portion of incident circularly-polarized optical energy into linearly-polarized optical energy.

The polarization rotator 402 and the polarization transformer 404 can be controlled such as to respectively provide rotation of the polarization state at a specified first rate and transformation of the polarization state at a specified second rate. Such a first rate can refer to a reciprocal of a duration over which the polarization is rotated from a first state to a second state, and the second rate can refer to a reciprocal of duration over which the polarization is transformed from a third state to a fourth state.

In this manner, the first detector 218 can be used to obtain information indicative of the optical energy reflected from the intravascularly-deliverable optical fiber transducer 100 during a first duration, the optical energy having a first polarization state or range of polarization states established by the polarization scrambler 400. The first detector 218 can also be used to obtain information indicative of the optical energy reflected from the intravascularly-deliverable optical fiber transducer 100 during a second duration, the optical energy having a second, different polarization state or range of polarization states established by the polarization scrambler 400. Information about the vibration, pressure, or strain modulating the optical energy from the intravascularly-deliverable optical fiber transducer can be processed, such as using the information obtained during the first and second durations. Such processing could include one or more of averaging or determining one or more other central tendencies of obtained information indicative of the reflected optical energy obtained from the optical fiber transducer.

In an illustrative example, a patient imaging guidewire can include assembling circumferentially, about an elongate cylindrical member such as a guidewire core (e.g., having a diameter of approximately 0.3556 millimeters), an array of thin optical fiber transducers (e.g., about 24 to about 36 optical fibers, each optical fiber having an outer diameter in a range of about 25 micrometers to about 30 micrometers, instead of a more typical telecommunication optical fiber outer diameter of about 125 micrometers), such as to provide an array of intravascularly-deliverable optical fiber transducers 100. As discussed above, an individual optical fiber transducer 100 can include an optical fiber core and an optical fiber cladding, with a refractive index or other optical properties specified to guide optical energy within the fiber assembly.

Respective optical fiber transducers included in the patient imaging guidewire can be coupled to a respective tunable optical sources and polarization scramblers. The respective optical fiber transducers can be selectively or controllably connected to the second optical source 208 (e.g., a higher powered "transmit" optical source that can be pulsed, as compared to a continuous-wave tunable optical source 204 that can be used as a "receive" source).

A 100 kilohertz (kHz) firing rate can be used for the second optical source 208 (e.g., the "transmit" source). For an imaging guidewire having an array including 32 intravascularly-deliverable optical fiber transducers, assuming that no two transducers are transmitting simultaneously, each element in the array can be fired at a repetition rate equivalent to about 3.125 kHz (corresponding to 100 kHz divided by 32 elements). At a repetition rate of about 3.125 kHz, 100 acquisitions of reflected optical energy can be acquired over a duration of about 32 milliseconds (ms), with such acquisitions including different respective polarization states of the optical energy established by the polarization scrambler 400.

Such a duration can be referred to as an "averaging period." If the polarization is to be rotated at least 10 times over the averaging period (e.g., 32 ms), the polarization rotator 402 (e.g., half-wavelength waveplate) can therefore use a first rate about 312.5 Hz or higher (e.g., 10 times the reciprocal of the measurement duration). Similarly, if one full polarization transformation is specified over the averaging period (e.g., 32 ms), the polarization transformer 404 (e.g., quarter-wavelength waveplate) can therefore use a second rate of about 31.25 Hz or higher. In this manner, an image or other information can be reconstructed for the received information at a frame rate of 30 Hz or more.

In general, the first rate (e.g., a rate of polarization rotation) can be higher than the second rate (e.g., a rate of polarization transformation), such as at least about five times higher. For example, the polarization rotator 402 can use a first rate of 1 kHz, and the polarization transformer 404 can use a second rate of 100 Hz.

For the illustrative example discussed above, such as for use with an ultrasonic imaging technique, the first and second rates are small with respect to an ultrasound energy center frequency. Such an ultrasound energy center frequency can range from about 5 MHz to about 50 MHz, or can include one or more other ranges, and in comparison, the first and second rates discussed above are in the range from tens of Hz to kHz. Therefore, the polarization state of the optical energy during a particular acquisition is roughly constant or only varies to a limited extent.

In contrast, in a pressure sensing example, the frequency range of information obtained from the reflected optical energy can overlap with the first and second polarization scrambling rates. A single acquisition of reflected optical energy can be during a duration over which a range of different polarization states are established by the polarization scrambler.

Figure 8:
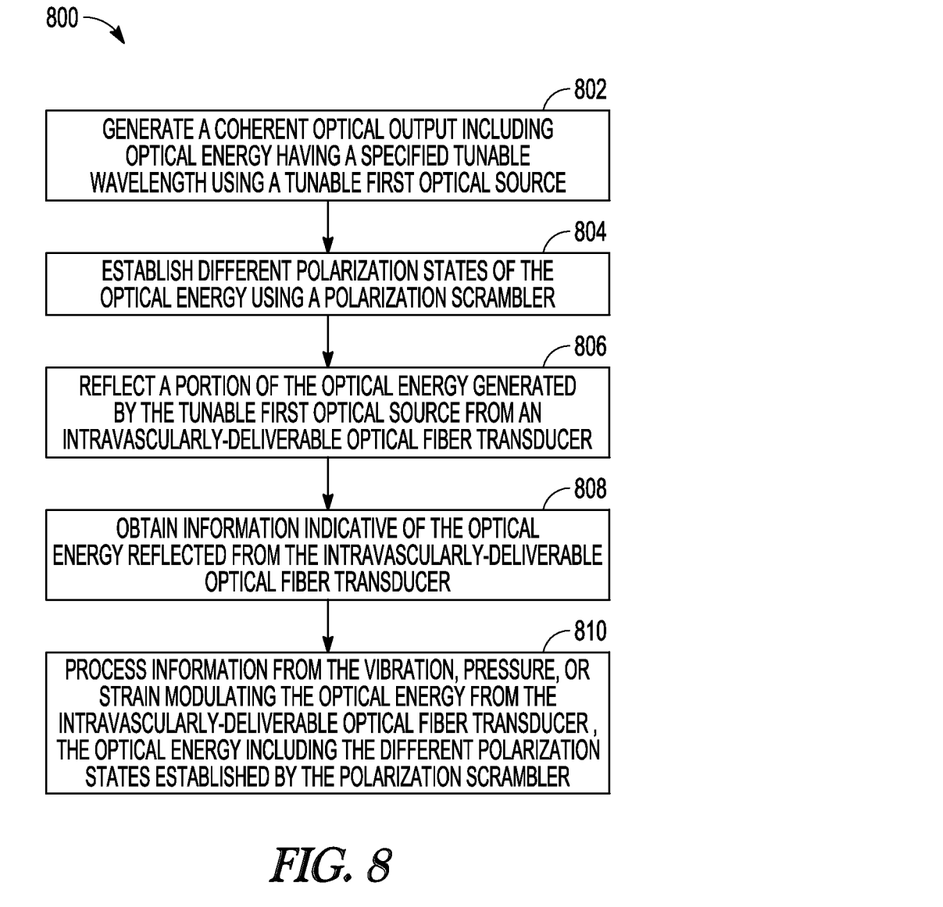
FIG. 8 illustrates generally a technique, such as a method, that can include establishing different polarization states of optical energy, such as using a polarization scrambler.

FIG. 8 illustrates generally a technique 800, such as a method, that can include establishing different polarization states of optical energy, such as using a polarization scrambler. FIG. 8 can include, or can be used with apparatus such as discussed elsewhere herein, such as in the examples of FIGS. 1A and 1B, FIG. 2, FIG. 4, or FIG. 7.

At 802, a coherent optical output can be generated such as including optical energy having a specified tunable wavelength, using a tunable first optical source. At 804, different polarization states of the optical energy can be established, such as using a polarization scrambler.

At 806, a portion of the optical energy generated by the tunable first optical source can be reflected from an intravascularly-deliverable optical fiber transducer, The optical energy can include the different polarization states established by the polarization scrambler, and the optical energy can be modulated in response to one or more of a vibration, pressure, or strain imparted on the intravascularly-deliverable optical fiber transducer.

At 808, information indicative of the optical energy reflected from the intravascularly-deliverable optical fiber transducer can be obtained, such as using an opto-electric detector (e.g., a diode detector).

At 810, information from the vibration, pressure, or strain modulating the optical energy from the intravascularly-deliverable optical fiber transducer can be processed. Such optical energy provided in response to incident optical energy including the different polarization states established by the polarization scrambler.

As discussed above, an array of optical fiber transducers can be used for acoustic imaging, such as by providing respective FBGs in the optical fiber cores at or near the distal end of an intravascularly-deliverable imaging guidewire assembly, and using the polarization scrambling techniques discussed in relation to FIG. 7, or elsewhere. Acoustic energy reflected back from the subject can be detected. Such acoustic energy detection can use an acoustic-to-optical transducer, such as using an optical signal that can be provided to an interferometer comprising FBGs (which need not be blazed) in the optical fiber core. A resulting acoustically-modulated optical signal can be communicated from the distal end of the guidewire imaging assembly to a proximal end of the guidewire imaging assembly such as for detection or further processing.

For example, the acoustically modulated optical energy can be optically coupled to an optical signal detection and signal processing apparatus that can be attached to a proximal end of the guidewire imaging assembly. The acoustically-modulated optical signal can be detected by an optical-to-electrical transducer and converted into an electrical signal. The resulting electrical signal can be signal-processed (along with signals from other optical fibers in the cylindrically-arranged array of optical fibers), such as using a phased array or synthetic aperture acoustic imaging technique, such as to produce an image of the region near a distal end of the guidewire assembly.

Various Notes & Examples

Each of the non-limiting examples included in this document can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An optical system, comprising:
a polarization scrambler configured to be coupleable to a tunable first optical source configured to generate a coherent optical output including optical energy having a specified tunable wavelength, the polarization scrambler including a polarization rotator and a polarization transformer, the polarization rotator configured to rotate at a first frequency and the polarization transformer configured to operate at a second frequency lower than the first frequency;
an intravascularly-deliverable optical fiber transducer configured to be coupled to a second optical source, the transducer configured to 1) convert optical energy from the second optical source to acoustic energy having an ultrasound energy center frequency, and 2) insonify a region of tissue using the acoustic energy,
the transducer further configured to be coupled to the tunable first optical source through the polarization scrambler, the polarization scrambler configured to vary a polarization state of the optical energy provided by the tunable first optical source, the intravascularly-deliverable optical fiber transducer configured to reflect a portion of the optical energy from the first optical source modulated in response to ultrasound, a vibration, pressure, or strain; and
a processor circuit configured to:
obtain and store information indicative of the modulated optical energy reflected from the intravascularly-deliverable optical fiber transducer during a first duration, the optical energy having a first polarization state or range of polarization states established by the polarization scrambler;

obtain and store information indicative of the modulated optical energy reflected from the intravascularly-deliverable optical fiber transducer during a second duration, the optical energy having a second, different polarization state or range of polarization states established by the polarization scrambler;

determine at least one central tendency of the stored information;

using the at least one determined central tendency, at least one of 1) determine one or more physiologic parameters and 2) construct an image of a physiologic region adjacent the insonified region of tissue, wherein the ultrasound energy center frequency has a range of about 5 megahertz to about 50 megahertz, and wherein at least one of the first and second frequencies has a range of about 10 hertz to 1 kilohertz.

2. The optical system of claim 1, wherein the polarization rotator is coupled to the tunable first optical source; and
wherein the polarization transformer is coupled between the polarization rotator and the intravascularly-deliverable optical fiber transducer.

3. The optical system of claim 1, wherein the polarization rotator comprises a half-wavelength waveplate configured to vary a polarization state of optical energy passing through the polarization rotator using the first frequency; and
wherein the polarization transformer comprises a quarter-wavelength waveplate configured to vary a polarization state of optical energy passing through the polarization transformer using the second frequency.

4. The optical system of claim 1, wherein the first frequency is about five times as large, or more, than the second frequency.

5. The optical system of claim 1, comprising:
an optical circulator coupled between the polarization scrambler and the first intravascularly-deliverable optical fiber transducer; and
a first optical detector coupled to the intravascularly-deliverable optical fiber transducer through the circulator and configured to provide information to the processor circuit, the information indicative of the optical energy reflected from the intravascularly-deliverable optical fiber transducer.

6. The optical system of claim 1, further comprising the tunable first optical source configured to generate the coherent optical output including optical energy having the specified tunable wavelength.

7. The optical system of claim 6, wherein the intravascularly-deliverable optical fiber transducer includes respective first and second optical fiber Bragg grating (FBG) structures, the first FBG structure located more proximally to the first optical source than the second FBG structure along the length of the intravascularly-deliverable optical fiber transducer, and the first and second FBG structures configured to define a first interferometer structure.

8. The optical system of claim 7, wherein the specified tunable wavelength provided by the first optical source is established by locking the first optical source to a transmission feature of the first interferometer structure.

9. The optical system of claim 8, wherein the specified tunable wavelength provided by the tunable first optical source is established by the locking the tunable first optical source to a wavelength about halfway along a transition between a relative minimum intensity of optical energy reflected from the interferometer structure and a wavelength corresponding to a relative maximum intensity of optical energy reflected from the first interferometer structure.

10. The optical system of claim 6, further comprising the second optical source configured to generate a coherent optical output including optical energy having a different wavelength than the wavelength provided by the first optical source,
wherein the reflected portion of the optical energy from a first sensor includes optical energy corresponding to ultrasonic vibration of the intravascularly-deliverable optical fiber sensor including ultrasonic energy reflected from the insonified region of tissue.

11. A method, comprising:
generating a coherent optical output including optical energy having a specified tunable wavelength using a tunable first optical source;

establishing different polarization states of the optical energy using a polarization scrambler, including varying a polarization state of the optical energy passing through a polarization rotator using a first frequency and varying a polarization state of the optical energy passing through a polarization transformer using a second frequency lower than the first frequency;

insonifying a region of tissue using acoustic energy via an intravascularly-deliverable optical fiber transducer coupled to a second optical source, wherein the transducer is configured to 1) convert optical energy from the second optical source to the acoustic energy having an ultrasound energy center frequency;

reflecting a portion of the optical energy generated by the tunable first optical source from the intravascularly-deliverable optical fiber transducer, the optical energy including the different polarization states established by the polarization scrambler, the optical energy modulated in response to ultrasound, a vibration, pressure, or strain imparted on the intravascularly-deliverable optical fiber transducer;

obtaining and storing information indicative of the modulated optical energy reflected from the intravascularly-deliverable optical fiber transducer during a first duration, the optical energy having a first polarization state or range of polarization states established by the polarization scrambler;

obtaining and storing information indicative of the modulated optical energy reflected from the intravascularly-deliverable optical fiber transducer during a second duration, the optical energy having a second, different polarization state or range of polarization states established by the polarization scrambler;

determining at least one central tendency of the stored information;

using the at least one determined central tendency, at least one of 1) determining one or more physiologic parameters and 2) constructing an image of a physiologic region adjacent the insonified region of tissue, wherein the ultrasound energy center frequency has a range of about 5 megahertz to about 50 megahertz, and wherein at least one of the first and second frequencies has a range of about 10 hertz to 1 kilohertz.

12. The method of claim 11, wherein the polarization rotator is coupled to the tunable first optical source; and
wherein the polarization transformer is coupled between the polarization rotator and the intravascularly-deliverable optical fiber transducer.

13. The method of claim 11, wherein the first frequency is about five times as large, or more, than the second frequency.

14. The method of claim 11, wherein the intravascularly-deliverable optical fiber transducer includes respective first and second optical fiber Bragg grating (FBG) structures, the first FBG structure located more proximally to the first optical source than the second FBG structure along the length of the intravascularly-deliverable optical fiber transducer, and the first and second FBG structures configured to define a first interferometer structure.

15. The method of claim 14, wherein the specified tunable wavelength provided by the first optical source is established by locking the first optical source to a transmission feature of the first interferometer structure.

16. The method of claim 15, wherein the specified tunable wavelength provided by the tunable first optical source is established by the locking the tunable first optical source to a wavelength about halfway along a transition between a relative minimum intensity of optical energy reflected from the interferometer structure and a wavelength corresponding to a relative maximum intensity of optical energy reflected from the first interferometer structure.

17. The method of claim 11, comprising:
coupling the intravascularly-deliverable optical fiber transducer to the second optical source;
generating a coherent optical output including optical energy having a different wavelength than the wavelength provided by the first optical source using the second optical source; and wherein a reflected portion of the optical energy generated by the tunable first optical source and reflected from the intravascularly-deliverable optical fiber transducer includes modulated optical energy corresponding to ultrasonic vibration of the intravascularly-deliverable optical fiber transducer including ultrasonic energy reflected from the insonified region of tissue.

18. An optical system, comprising:
an intravascularly-deliverable optical fiber transducer including an interferometer structure configured to reflect a proportion of incident optical energy for a range of wavelengths;
a tunable optical source configured to generate a coherent optical output including optical energy having a specified tunable wavelength, wherein the specified tunable wavelength is established by locking the tunable optical source to a wavelength about halfway along a transition between a relative minimum intensity of optical energy reflected from the interferometer structure and a wavelength corresponding to a relative maximum intensity of optical energy reflected from the interferometer structure;
a polarization scrambler configured to be coupleable to the tunable optical source, the polarization scrambler including a polarization rotator and a polarization transformer, the polarization rotator configured to rotate at a first frequency and the polarization transformer configured to operate at a second frequency lower than the first frequency;
wherein the intravascularly-deliverable optical fiber transducer is configured to be coupled to a second optical source, the transducer configured to 1) convert optical energy from the second optical source to acoustic energy having an ultrasound energy center frequency and 2) insonify a region of tissue using the acoustic energy,
the transducer further configured to be coupled to the tunable optical source through the polarization scrambler, the polarization scrambler configured to vary a polarization state of the optical energy provided by the tunable optical source, the intravascularly-deliverable optical fiber transducer configured to reflect a portion of the optical energy from the first optical source modulated in response to ultrasound, a vibration, pressure, or strain;
a processor circuit configured to:
obtain and store information indicative of the modulated optical energy reflected from the intravascularly-deliverable optical fiber transducer during a first duration, the optical energy having a first polarization state or range of polarization states established by the polarization scrambler;
obtain and store information indicative of the modulated optical energy reflected from the intravascularly-deliverable optical fiber transducer during a second duration, the optical energy having a second, different polarization state or range of polarization states established by the polarization scrambler;
determine at least one central tendency of the stored information;
using the at least one determined central tendency, at least one of 1) determine one or more physiologic parameters and 2) construct an image of a physiologic region adjacent the insonified region of tissue,
wherein the ultrasound energy center frequency has a range of about 5 megahertz to about 50 megahertz, and
wherein at least one of the first and second frequencies has a range of about 10 hertz to 1 kilohertz.

19. A method, comprising:
generating a coherent optical output including optical energy having a specified tunable wavelength using a tunable optical source;
establishing different polarization states of the optical energy using a polarization scrambler, the polarization scrambler including a polarization rotator and a polarization transformer, wherein establishing different polarization states includes rotating the polarization rotator at a first frequency and rotating the polarization transformer at a second frequency lower than the first frequency rate is higher than the second frequency;
insonifying a region of tissue using an intravascularly-deliverable optical fiber transducer coupled to a second optical source, wherein the transducer is configured to 1) convert optical energy from the second optical source to the acoustic energy having an ultrasound energy center frequency;
reflecting a portion of the optical energy generated by the tunable optical source from the intravascularly-deliverable optical fiber transducer, the optical energy including the different polarization states established by the polarization scrambler, the optical energy modulated in response to ultrasound, a vibration, pressure, or strain imparted on the intravascularly-deliverable optical fiber transducer;
obtaining and storing information indicative of the modulated optical energy reflected from the intravascularly-deliverable optical fiber transducer during a first duration, the optical energy having a first polarization state or range of polarization states established by the polarization scrambler;
obtaining and storing information indicative of the modulated optical energy reflected from the intravascularly-deliverable optical fiber transducer during a second duration, the optical energy having a second, different polarization state or range of polarization states established by the polarization scrambler;

determining at least one central tendency of the stored information;
using the at least one determined central tendency, at least one of 1) determining one or more physiologic parameters and 2) constructing an image of a physiologic region adjacent the insonified region of tissue,
wherein the ultrasound energy center frequency has a range of about 5 megahertz about 50 megahertz, and
wherein at least one of the first and second frequencies has a range of about 10 hertz to 1 kilohertz.

* * * * *

UNITED STATES PATENT AND TRADEMARK OFFICE
CERTIFICATE OF CORRECTION

PATENT NO. : 9,936,881 B2  
APPLICATION NO. : 14/045189  
DATED : April 10, 2018  
INVENTOR(S) : Rourke et al.

Page 1 of 1

It is certified that error appears in the above-identified patent and that said Letters Patent is hereby corrected as shown below:

On the Title Page

On page 2, in Column 2, under "Other Publications", Line 17, delete "Respose" and insert --Response-- therefor In the Specification In Column 5, Line 32, delete "FIG." and insert --FIGS.-- therefor In Column 7, Line 7, delete "504," and insert --502,-- therefor In the Claims

In Column 13, Line 52, in Claim 7, delete "fiber Bragg grating" and insert --Fiber Bragg Grating-- therefor In Column 15, Line 3, in Claim 14, delete "fiber Bragg grating" and insert --Fiber Bragg Grating-- therefor In Column 15, Line 27, in Claim 17, after "and", insert --¶--

In Column 17, Line 8, in Claim 19, after "megahertz", insert --to--

Signed and Sealed this  
Fourth Day of June, 2019

Andrei Iancu  
*Director of the United States Patent and Trademark Office*